(12) United States Patent  (10) Patent No.: US 8,571,648 B2
Anderson et al.  (45) Date of Patent: Oct. 29, 2013

(54) APPARATUS AND METHOD TO APPLY SUBSTANCES TO TISSUE

(75) Inventors: Robert S. Anderson, Livermore, CA (US); Steve Young, Discovery Bay, CA (US)

(73) Assignee: Aesthera, Livermore, CA (US)

( * ) Notice: Subject to any disclaimer, the term of this patent is extended or adjusted under 35 U.S.C. 154(b) by 2482 days.

(21) Appl. No.: 11/123,599

(22) Filed: May 6, 2005

(65) Prior Publication Data

US 2006/0189964 A1 Aug. 24, 2006

Related U.S. Application Data

(63) Continuation-in-part of application No. 11/024,340, filed on Dec. 27, 2004, now Pat. No. 7,842,029, which is a continuation-in-part of application No. 10/841,273, filed on May 7, 2004.

(51) Int. Cl.
*A61B 18/20* (2006.01)

(52) U.S. Cl.
USPC ........ 604/20; 606/9; 606/10; 606/13; 606/33; 607/88; 607/91

(58) Field of Classification Search
USPC ............ 606/2–19, 33–34; 607/2, 88–94, 104; 604/20
See application file for complete search history.

(56) References Cited

U.S. PATENT DOCUMENTS 3,674,031 A 7/1972 Weiche
(Continued)

FOREIGN PATENT DOCUMENTS

AU 55604/86 10/1987
EP 0784997 7/1997
(Continued)

OTHER PUBLICATIONS

PCT Notification of Transmittal of the International Search Report and the Written Opinion of the International Searching Authority or the Declaration; the PCT International Search Report and Written Opinion for PCT International Appln No. PCT/US2006/017948, mailed Oct. 25, 2007. (19 pages).

(Continued)

*Primary Examiner* — David Shay
(74) *Attorney, Agent, or Firm* — Wood, Herron & Evans LLP

(57) ABSTRACT

Methods and apparatuses to apply substances to a biological tissue are described. The tissue having an target below a surface is stretched to provide openings in a surface. Stretching forces a material from the target onto the surface. A first substance may be applied while stretching to promote cleaning the tissue. A second substance may be applied to the surface. Energy may be applied to the tissue. Then the tissue is relaxed to draw the second substance through the openings into the tissue. The tissue may be stretched by applying a negative pressure, and relaxed by removing the negative pressure. The first substance may be an abrasive material. The second substance is a medicine, a moisturizer, a lotion, or any combination thereof. The second substance may be applied to the biological tissue using a positive pressure. The apparatus to apply substances may be a handheld device.

26 Claims, 18 Drawing Sheets

(56) References Cited

U.S. PATENT DOCUMENTS

| | | | |
|---|---|---|---|
| 3,712,306 A | 1/1973 | Bryne | |
| 3,794,039 A | 2/1974 | Kollner et al. | |
| 3,862,627 A | 1/1975 | Hans, Sr. | |
| 4,388,924 A | 6/1983 | Weissman et al. | |
| 4,562,838 A | 1/1986 | Walker | |
| 4,573,970 A | 3/1986 | Wagner | |
| 4,600,403 A | 7/1986 | Wagner | |
| 4,733,660 A * | 3/1988 | Itzkan | 606/9 |
| 4,742,235 A | 5/1988 | Koji | |
| 4,837,049 A | 6/1989 | Byers et al. | |
| 5,000,752 A | 3/1991 | Hoskin et al. | |
| 5,057,104 A | 10/1991 | Chess | |
| 5,059,192 A | 10/1991 | Zaias | |
| 5,171,215 A * | 12/1992 | Flanagan | 604/22 |
| 5,226,907 A | 7/1993 | Tankovich | |
| 5,405,368 A | 4/1995 | Eckhouse | |
| 5,441,498 A | 8/1995 | Perkins | |
| 5,449,378 A | 9/1995 | Schouenborg | |
| 5,519,534 A | 5/1996 | Smith et al. | |
| 5,595,568 A | 1/1997 | Anderson et al. | |
| 5,626,631 A | 5/1997 | Eckhouse | |
| 5,674,267 A | 10/1997 | Mir et al. | |
| 5,707,349 A | 1/1998 | Edwards | |
| 5,735,844 A | 4/1998 | Anderson et al. | |
| 5,824,023 A | 10/1998 | Anderson | |
| 5,853,407 A | 12/1998 | Miller | |
| 5,964,749 A | 10/1999 | Eckhouse et al. | |
| 6,048,352 A | 4/2000 | Douglas et al. | |
| 6,071,239 A | 6/2000 | Cribbs et al. | |
| 6,162,218 A * | 12/2000 | Elbrecht et al. | 606/41 |
| 6,168,590 B1 | 1/2001 | Neev | |
| 6,187,001 B1 | 2/2001 | Azar et al. | |
| 6,273,884 B1 | 8/2001 | Altshuler et al. | |
| 6,277,116 B1 | 8/2001 | Utely et al. | |
| 6,280,438 B1 | 8/2001 | Eckhouse et al. | |
| 6,315,772 B1 | 11/2001 | Marchitto et al. | |
| 6,355,054 B1 | 3/2002 | Neuberger | |
| 6,387,089 B1 | 5/2002 | Kreindel et al. | |
| 6,387,380 B1 | 5/2002 | Knowlton | |
| 6,402,739 B1 * | 6/2002 | Neev | 606/9 |
| 6,416,514 B1 | 7/2002 | Ein-Gal | |
| 6,438,424 B1 | 8/2002 | Knowlton | |
| 6,461,348 B1 | 10/2002 | Bertan | |
| 6,461,354 B1 | 10/2002 | Olsen et al. | |
| 6,508,813 B1 | 1/2003 | Altshuler | |
| 6,511,475 B1 | 1/2003 | Altshuler et al. | |
| 6,514,243 B1 | 2/2003 | Eckhouse et al. | |
| 6,517,532 B1 | 2/2003 | Altshuler et al. | |
| 6,595,934 B1 | 7/2003 | Hissong et al. | |
| 6,605,080 B1 | 8/2003 | Altshuler et al. | |
| 6,662,054 B2 | 12/2003 | Kreindel et al. | |
| 6,749,624 B2 | 6/2004 | Knowlton | |
| 6,766,202 B2 | 7/2004 | Underwood et al. | |
| 6,835,184 B1 | 12/2004 | Sage et al. | |
| 7,025,765 B2 | 4/2006 | Balbierz et al. | |
| 7,108,689 B2 | 9/2006 | Eckhouse et al. | |
| 7,250,047 B2 | 7/2007 | Anderson | |
| 7,643,883 B2 | 1/2010 | Kreindel | |
| 2001/0025190 A1* | 9/2001 | Weber et al. | 607/89 |
| 2002/0049483 A1 | 4/2002 | Knowlton | |
| 2002/0169442 A1 | 11/2002 | Neev | |
| 2003/0125649 A1* | 7/2003 | McIntosh et al. | 601/15 |
| 2003/0167032 A1* | 9/2003 | Ignon | 604/19 |
| 2003/0199859 A1* | 10/2003 | Altshuler et al. | 606/9 |
| 2004/0082940 A1 | 4/2004 | Black et al. | |
| 2004/0151671 A1* | 8/2004 | Abram et al. | 424/45 |
| 2004/0193218 A1* | 9/2004 | Butler | 607/1 |
| 2005/0049543 A1 | 3/2005 | Anderson et al. | |
| 2005/0049583 A1 | 3/2005 | Swanson | |
| 2005/0215987 A1 | 9/2005 | Slatkine | |
| 2005/0222555 A1 | 10/2005 | Manstein et al. | |
| 2005/0234527 A1 | 10/2005 | Slatkine | |
| 2005/0245923 A1 | 11/2005 | Christopherson et al. | |
| 2005/0251117 A1 | 11/2005 | Anderson | |
| 2005/0251118 A1 | 11/2005 | Anderson | |
| 2006/0058714 A1 | 3/2006 | Rhoades | |
| 2006/0189964 A1 | 8/2006 | Anderson | |
| 2006/0253178 A1 | 11/2006 | Masotti | |
| 2006/0259102 A1 | 11/2006 | Slatkine | |
| 2007/0010861 A1 | 1/2007 | Anderson et al. | |
| 2007/0055180 A1 | 3/2007 | Deem et al. | |
| 2007/0060989 A1 | 3/2007 | Deem et al. | |
| 2007/0142885 A1 | 6/2007 | Hantash et al. | |
| 2007/0179482 A1 | 8/2007 | Anderson | |
| 2007/0185432 A1 | 8/2007 | Etheredge, III et al. | |
| 2007/0208340 A1 | 9/2007 | Ganz et al. | |
| 2007/0213705 A1 | 9/2007 | Schmid | |
| 2008/0065176 A1 | 3/2008 | Zhang et al. | |
| 2008/0082090 A1 | 4/2008 | Manstein et al. | |
| 2008/0200910 A1 | 8/2008 | Burger | |
| 2008/0287943 A1 | 11/2008 | Weber et al. | |
| 2009/0005801 A1 | 1/2009 | Eastman | |
| 2009/0012434 A1 | 1/2009 | Anderson | |
| 2009/0069795 A1 | 3/2009 | Anderson | |
| 2009/0076497 A1 | 3/2009 | Morris et al. | |
| 2009/0093864 A1 | 4/2009 | Anderson | |

FOREIGN PATENT DOCUMENTS

| | | |
|---|---|---|
| EP | 0806913 | 6/2002 |
| EP | 1338263 A2 | 8/2003 |
| FR | 2667 247 A | 4/1991 |
| GB | 2378392 | 2/2003 |
| GB | 2369057 | 2/2006 |
| IL | 147009 | 12/2001 |
| IL | 150094 | 6/2002 |
| IL | 160510 | 2/2004 |
| JP | 48-5296 | 1/1973 |
| JP | 9-028448 | 2/1997 |
| JP | 9-253193 | 9/1997 |
| WO | WO-86/01728 | 3/1986 |
| WO | WO 96/23447 | 8/1996 |
| WO | WO 02094116 A | 11/2002 |
| WO | WO 03/049633 | 6/2003 |
| WO | WO-03/079916 | 10/2003 |
| WO | WO 03/096919 A | 11/2003 |
| WO | WO 2004007022 A | 1/2004 |
| WO | WO 2004037068 A | 5/2004 |
| WO | WO 2005/082435 A | 9/2005 |
| WO | WO-2006/012752 | 2/2006 |
| WO | WO-2006/031632 | 3/2006 |
| WO | PCT/IL2006/000897 | 8/2006 |
| WO | WO-2006/093384 | 9/2006 |
| WO | WO 2006/122136 | 11/2006 |
| WO | WO 2007/015247 | 2/2007 |

OTHER PUBLICATIONS

Derwent Publication Ltd. London GB; AN 2005-804121 XP002414902 & JP 2005 334188 A (Eiburu KK) Dec. 8, 2005 Abstract (Total 1 page).

L.L. Polla, et al. "Melanosomes are a primary target of Q-switched ruby laser irradiation in guinea pig skin", *Journal of Investigative Dermatology*, 89, pp. 281-286, 1987.

Fay, et al. *Three Approaches for Estimating the Elastic Modulus of the Tympanic Membrane*, Journal of Biomechanics 38 (2005) pp. 1807-1815 (8 pages).

Goh, et al. *Stress Transfer in Collagen Fibrils Reinforcing Connective Tissues: Effects of Collagen Fibril Slenderness and Relative Stiffness*, The Journal of Theoretical Biology, vol. 245 (2007) pp. 305-311 (6 pages).

PCT International Preliminary Report on Patentablility and Written Opinion of the International Searching Authority for PCT/US2005/015126, International filing date Apr. 29, 2005, mailing date Nov. 16, 2006 (12 pages).

PCT International Preliminary Report on Patentability and Written Opinion of the International Searching Authority for PCT/US2005/015131, International filing date Apr. 29, 2005, mailing date Nov. 16, 2006 (11 pages).

PCT International Search Report and PCT Written Opinion for PCT International Appln No. US2005/015126, mailed Jul. 26, 2005 (18 pages).

(56) References Cited

OTHER PUBLICATIONS

PCT Search Report and PCT Written Opinion for PCT International Appln No. PCT/US2005/015131, mailed Dec. 20, 2005 (18 pages).
PCT Written Opinion of the International Searching Authority for PCT International Appln No. PCT/US2006/017948, mailed May 27, 2008. (13 pages).
Polla, L. et al. Melanosomes are a primary target of Q-switched ruby laser irradiation in guinea pig skin, *Journal of Investigative Dermatology*, 89, pp. 281-286, 1987 (6 pages).
Sasaki, et al. *Stress-Strain Curve and Young's Modulus of a Collagen Molecule as Determined by the X-Ray Diffraction Technique*, J. Biomechanix, vol. 29, No. (5 pages).
Yang, et al. *Micromechanical Bending of Single Collagen Fibrils Using Atomic Force Microscopy*, 2007 Wiley Periodicals, Published online Jan. 31, 2007 in Wiley InterScience (www.interscience.wiley.com) DOI: 10.1002/jbm.a.31127, pp. 160-168 (9 pages).
PCT Search Report and Written Opinion for PCT International Appln No. PCT/US2005/015131, mailed Dec. 20, 2005. (18 pages).
"PCT International Preliminary Report on Patentability and Written Opinion", PCT/US2006/017948, P002XPCT, (Nov. 29, 2007), 11.
"PCT International Preliminary Report on Patentability", PCT/US2008/004101, 6983P001X2PCT mailed Oct. 15, 2009, 9.
"PCT International Search Report and Written Opinion", PCT/US2008/004101, P001X2PCT, (Dec. 3, 2008), 17.
"PCT Invitation to Pay Additional Fees", PCT/US2008/004101, P001X2PCT, (Aug. 12, 2008), 5.
"PCT Invitation to Pay Additional Fees", PCT/US2006/017948, P002XPCT, (Jun. 18, 2007), 6.
"PCT Invitation to Pay Additional Fees", PCT/US2005/015131, P001PCT, (Aug. 5, 2005), 8.

* cited by examiner

210
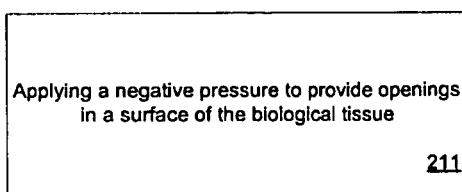
Applying a negative pressure to provide openings in a surface of the biological tissue
211
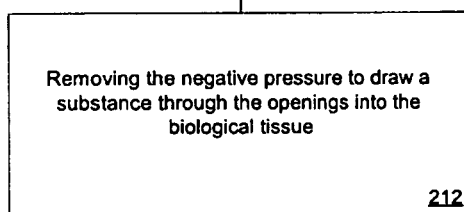
Removing the negative pressure to draw a substance through the openings into the biological tissue
212
FIG. 2B

600

Applying a negative pressure to a biological tissue having a surface and a target under the surface, to push out at least a portion of a material from the target onto the surface

601

Applying a substance to the surface while stretching to promote cleaning the biological tissue

```
┌─────────────────────────────────┐
│ Stretching a biological tissue having a surface │
│ to provide openings in the surface of the │
│ biological tissue │
│                             701 │
└─────────────────────────────────┘
                 │
┌─────────────────────────────────┐
│ Applying a substance to the surface while │
│ stretching to promote cleaning of the │
│ biological tissue │
│                             702 │
└─────────────────────────────────┘
```

```
┌─────────────────────────────────────────────┐
│ Applying a negative pressure to provide     │
│ openings in a surface of the biological     │
│ tissue                                      │
│                                         901 │
└─────────────────────────────────────────────┘
                      │
┌─────────────────────────────────────────────┐
│ Exposing the surface to a first substance   │
│ while stretching to promote cleaning        │
│ (e.g., exfoliation) of the surface          │
│                                         902 │
└─────────────────────────────────────────────┘
                      │
┌─────────────────────────────────────────────┐
│ Applying a second substance to the surface  │
│                                         903 │
└─────────────────────────────────────────────┘
                      │
┌─────────────────────────────────────────────┐
│ Removing the negative pressure to push the  │
│ second substance through the openings into  │
│ the biological tissue                       │
│                                         904 │
└─────────────────────────────────────────────┘
```

FIG. 9

APPARATUS AND METHOD TO APPLY SUBSTANCES TO TISSUE

RELATED APPLICATIONS

The present application is a Continuation-In-Part to U.S. patent application Ser. No. 10/841,273 filed on May 7, 2004 and to U.S. patent application Ser. No. 11/024,340, filed on Dec. 27, 2004.

FIELD

The present invention relates to treatment of tissue, and more specifically, to applying substances to biological tissue.

BACKGROUND

The skin may be considered to be the largest and most visible kind of biological tissue of the human body. It reflects the health of the body and acts as a barrier against injury and bacteria. Numerous invasive and non-invasive techniques are used for treating or diagnosing a condition of a skin. The invasive techniques require incisions and suturing of the skin. The non-invasive techniques treat the skin therapeutically that preserves the tissue from incisions and suturing. The non-invasive techniques may use various substances or energy from various regions of the electromagnetic spectrum, such as light, ultrasound, radio frequency, to treat the skin.

In recent years, the technologies, which use various light sources, to treat skin conditions, have been commercialized into numerous devices that remove unwanted hair, wrinkles, fine lines and various facial blemishes, tattoos, and vascular and pigmented lesions. The light, when applied directly to the human body, is absorbed by the various targets, for example, hemoglobin in the blood; the water in the skin; the melanin in the skin; or by the melanin in the hair follicles, depending on the wavelength of the light used and properties of the targets. Therefore, lasers generating coherent, monochromatic light were found early on to have different properties, each being preferable for specific procedures. In addition to lasers, several manufacturers have also introduced devices using broadband sources, which emit light of a range of wavelengths that practitioners then filter to select the appropriate wavelength for a specific treatment. Typically, with conventional skin treatment technologies there is a very fine line between effectiveness and collateral damage of the skin. Generally, light of shorter wavelengths has higher absorption efficiency. For example, blue and green light is highly absorbed not only by a target, but also by the tissue surrounding a target, which impacts the effectiveness of the treatment. Traditional lasers and light based systems require more power to compensate for the loss of the light due to reflection, scattering and absorption by the surrounding tissue that rises a risk of collateral damage of the surrounding tissue.

FIG. 1 is a diagram 100 illustrating the skin. As shown in FIG. 1, the outer most layer of the skin is epidermis 101, which covers dermis 102. The thickness of epidermis 101 is typically between 50 to 100 microns. As shown in FIG. 1, epidermis 101, dermis 102 and subcutaneous tissue 103 contain potential targets, e.g., hair follicles, dermal vessels, and pigmentary lesions, for therapy. As shown in FIG. 1, dermis 102 contains sebaceous gland 104, hair bulbs 105, and nerve endings 106. Sebaceous glands 104 secrete an oily substance called sebum. In humans, sebaceous glands 104 are primarily found in association with hair follicles but also occur in hairless areas of the skin. Sebum is a mixture of fat and the debris of dead fat-producing cells. These cells are constantly replaced by new growth at the base of the glands. Generally the sebum is deposited on the hair inside the follicles and is brought up to the surface of the skin along the hair shaft 110. In hairless areas, the sebum may surface through ducts. Sebum lubricates and protects the hair and skin and prevents drying and irritation of membranes. Excessive secretions of sebum may be related to acne, certain forms of baldness, and other skin disorders. As shown in FIG. 1, sebaseous glands 104 is covered by the epidermis 101 that complicates an access to the sebaseous glands 104. For example, one of the problems with current methods of applying medicines to treat acne is the difficulty of getting the medicine into the sebaceous gland. In addition, extraction of sebum directly from the sebaseous glands 104 is complicated.

As shown in FIG. 1, subcutaneous tissue 103 contains blood vessels 107, sweat glands 108, and cutaneous nerves 109. Blood vessels 107 provide nourishment to the overlying epidermis 101. The layers of the epidermis 101 may be peeled off using chemical or mechanical means to treat scarring, lines, wrinkles, sun damage, pigmentation disorders and certain types of skin lesions. The peeling off the layers of epidermis 101 refers to a skin resurfacing technique, e.g., a microdermabrasion technique, which uses tiny crystals of an abrasive material to peel off the layers of epidermis 101.

Conventional therapeutic technologies, however, may be inefficient in delivering energy or substance to a target due to the substantial loss of the energy or substance in the surrounding tissue and competing dermal and epidermal elements. In addition, conventional therapeutic technologies may require large amounts of energy or substance to treat the skin that compromises epidermal safety and the patient's comfort.

SUMMARY OF THE DESCRIPTION

Methods and apparatuses to apply substances to treat a biological tissue are described. The biological tissue having a substance on a surface of the biological tissue is stretched to provide openings in the surface. Then the biological tissue is relaxed to draw the substance through the openings from the surface into the biological tissue. The stretching may be performed by applying a pressure, which is less than atmospheric pressure, (which may be referred to as "negative pressure"), e.g., a vacuum, to the biological tissue. The relaxing may be performed by removing the negative pressure from the biological tissue. The substance may be applied onto the surface of the biological tissue by using a pressure higher than atmospheric pressure ("positive pressure"). Energy may be provided to the biological tissue while stretching is performed. The energy may be a light, a radio frequency, an ultrasound, or any combination thereof. The substance will typically include a carrier fluid (e.g., water) and a medicinal ingredient. The carrier fluid, at least in certain embodiments, is not designed to evaporate in significant portions when the negative pressure is applied. In other embodiments, the carrier fluid may evaporate, while under a vacuum, thereby causing evaporative cooling on the surface of the biological tissue. This may be useful in cases where the application of energy, such as light, will tend to heat the surface.

The stretching of the biological tissue may expose an inner surface of a target below the surface of the biological tissue. The stretching may push a material (e.g., a debris) contained in the target through the openings onto the surface of the biological tissue to clean the target. The relaxing may draw the substance applied to the surface into the target.

In one embodiment, stretching a biological tissue having a surface and a target below the surface is performed, to provide openings in the surface. In one embodiment, the stretching is performed by applying a negative pressure to the biological tissue. The stretching exposes debris in the openings of the biological tissue. Next, a first substance is applied to the surface while the biological tissue is stretched to promote cleaning of the surface. In one embodiment, the first substance is an abrasive material. Next, a second substance is applied to the biological tissue. In one embodiment, the second substance is a medicine, moisturizer, lotion, or any combination thereof. Then the biological tissue is relaxed to draw the second substance through the openings into the biological tissue. In one embodiment, the relaxing is performed by removing a negative pressure from the biological tissue. In one embodiment, the apparatus to apply substances to treat the biological tissue is a standalone device. In another embodiment, the apparatus to apply substances to the biological tissue is incorporated into an existing device. In one embodiment, the apparatus to apply substances is a handheld device.

BRIEF DESCRIPTION OF THE DRAWINGS

The present invention is illustrated by way of example and not limitation in the figures of the accompanying drawings in which like references indicate similar elements.

FIG. 2B is a flowchart of another embodiment of a method to treat a biological tissue.

FIG. 6 is a flowchart of one embodiment of a method to clean a biological tissue.

FIG. 7 is a flowchart 700 of another embodiment of a method to clean a biological tissue.

FIG. 9 is a flowchart of another embodiment of a method to treat a biological tissue.

DETAILED DESCRIPTION

The subject invention will be described with reference to numerous details set forth below, and the accompanying drawings will illustrate the invention. The following description and drawings are illustrative of the invention and are not to be construed as limiting the invention. Numerous specific details are described to provide a thorough understanding of the present invention. However, in certain instances, well known or conventional details are not described in order to not unnecessarily obscure the present invention in detail.

Reference throughout the specification to "one embodiment", "another embodiment", or "an embodiment" means that a particular feature, structure, or characteristic described in connection with the embodiment is included in at least one embodiment of the present invention. Thus, the appearance of the phrases "in one embodiment" or "in an embodiment" in various places throughout the specification are not necessarily all referring to the same embodiment. Furthermore, the particular features, structures, or characteristics may be combined in any suitable manner in one or more embodiments.

Figure 1:
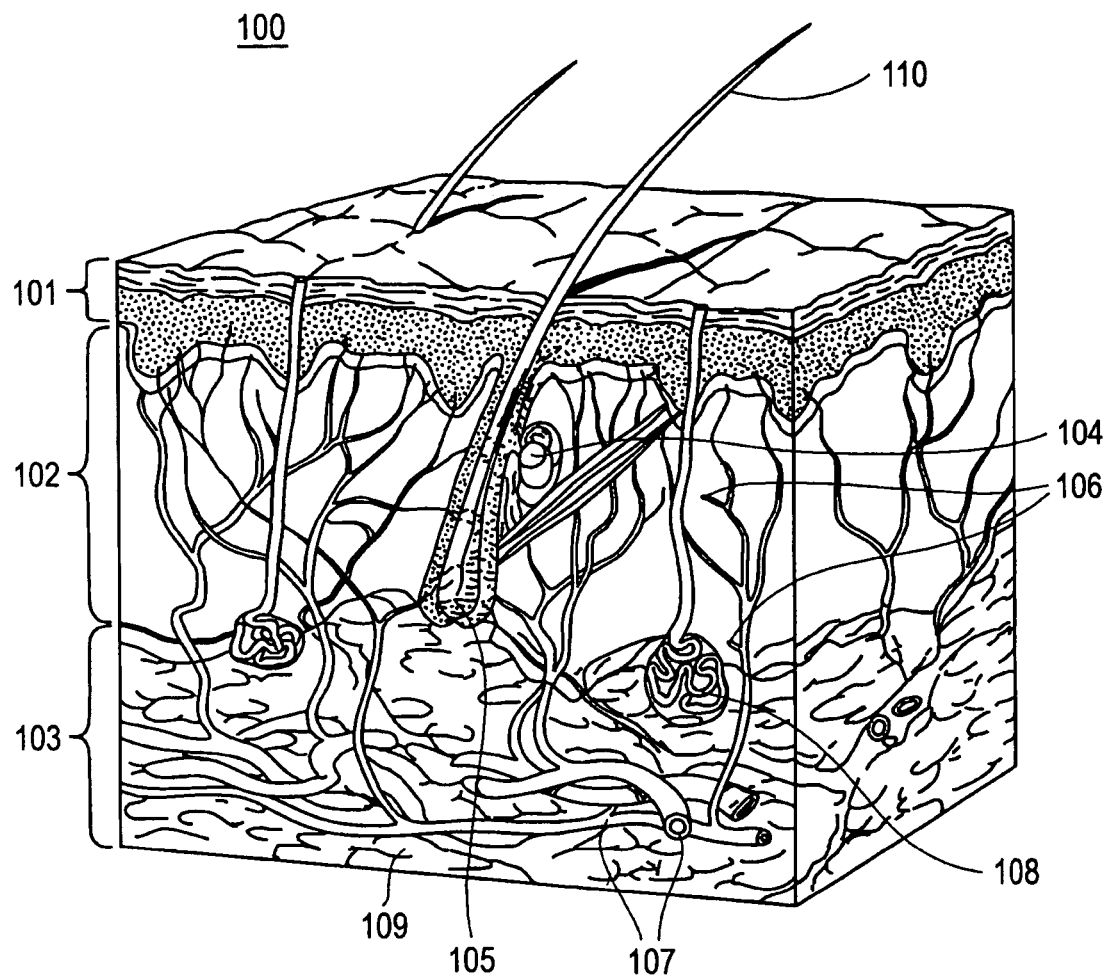
FIG. 1 is a three-dimensional diagram illustrating a skin.
Figure 2A:
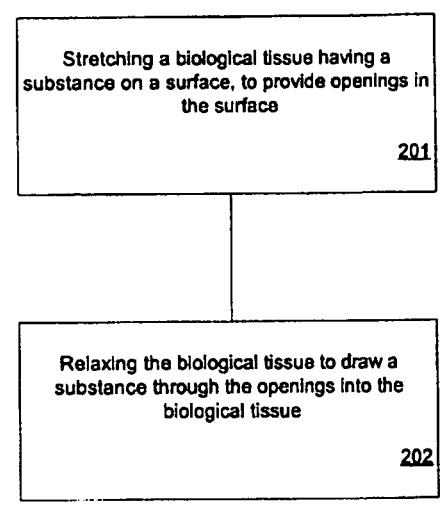
FIG. 2A is a flowchart of one embodiment of a method to treat a biological tissue.

FIG. 2A is a flowchart 200 of one embodiment of a method to treat a biological tissue. The method begins with operation 201 of stretching the biological tissue having a substance on a surface of the biological tissue. In one embodiment, a pressure, which is lower than atmospheric pressure ("negative pressure"), for example, a vacuum, may be applied to the surface to stretch the biological tissue. In alternate embodiments, the biological tissue may be stretched using one of various techniques known to one of ordinary skill in the art of treatment of the biological tissue, e.g., the biological tissue may be stretched mechanically. The method continues with operation 202 of relaxing the biological tissue to draw the substance from the surface into the biological tissue. In one embodiment, the biological tissue may be relaxed by removing the negative pressure applied to the surface of the biological tissue. In alternate embodiment, the biological tissue may be relaxed by removing the stretching using techniques known to one of ordinary skill in the art of treatment of the biological tissue. In an embodiment, operations 201 and 202 may be repeated multiple times on the same area. The substance, at least in certain embodiments, will typically include a carrier fluid (e.g. water, an alcohol) and one or more medical ingredients dissolved or dispersed in the carrier fluid. Examples of medical ingredients include medicines for a hair treatment e.g., as listed on a website http://www.hairsite.com/topical/t-alpha.htm, such as crinagen, azelaic acid, retin A, minoxidil, etc.; medicines for a psoriasis treament e.g., as listed on a website http://www.psoriasis.org/treatment/psoriasis/topicals.php such as various steroids, coal tar, calcipotriene, anthralin, etc.; medicines for an acne or rosacea treatment e.g., as listed on a website http://dermatology.about.com/cs/topicals/a/topicalacne_3.htm such as benzoyl peroxide, salicyclic acid, azelaic acid, sulfacetamide-sulfur, erythromycin, etc.; medicines to treat photo aged skin e.g., as listed on a website http://www.postgradmed.com/issues/1997/08_97/kligman.htm, such as retinoids, antioxidants, alpha hydroxy acids, etc.; topical antispectics, as listed e.g., on a website http://www.reproline.jhu.edu/video/hiv/tutorials/English/tutorials/IP/references/pdf/I P_manual/B_Antispectics.pdf#search='antiseptics, such as various alcohol solutions, including ethyl alcohol, isopropyl alcohol, or methylated spirit, clophexidine, iodine and iodophor prepartions, para-chlorometexylenol, triconsan, etc.; medicines for wrinkle treatment e.g.; as listed on a website http://scarheal.com/?OVRAW=topical%20wrinkle%20treatment&OVKEY=scar%20tuck%20tummy&OVMTC= advanced, various photoactivated compounds, vitamins, such as vitamins C, A, D, and E, herbal extracts, coenzymes, silicone dioxide, etc. The carrier fluid will normally be compatible with the medicinal ingredient. For example, if the medicinal ingredient is hydrophobic (e.g., a lipid based composition) then the carrier fluid may be hydrophobic or amphiphilic. The carrier fluid may be inert relative to the medicinal ingredient, which is carried by the carrier fluid. Further, at least in certain embodiments, the carrier fluid is not designed to evaporate, in significant portions, when the negative pressure (e.g., a partial vacuum) is applied to stretch the skin.

FIG. 2B is a flowchart 210 of another embodiment of a method to treat a biological tissue. The method begins with operation 211 of applying a negative pressure to the biological tissue to provide openings in a surface of the biological tissue, wherein a substance is deposited over or to be deposited over the biological tissue while it si stretched. The method continues with operation 212 of removing the negative pressure to draw the substance through the openings into the biological tissue.

Figure 3A:
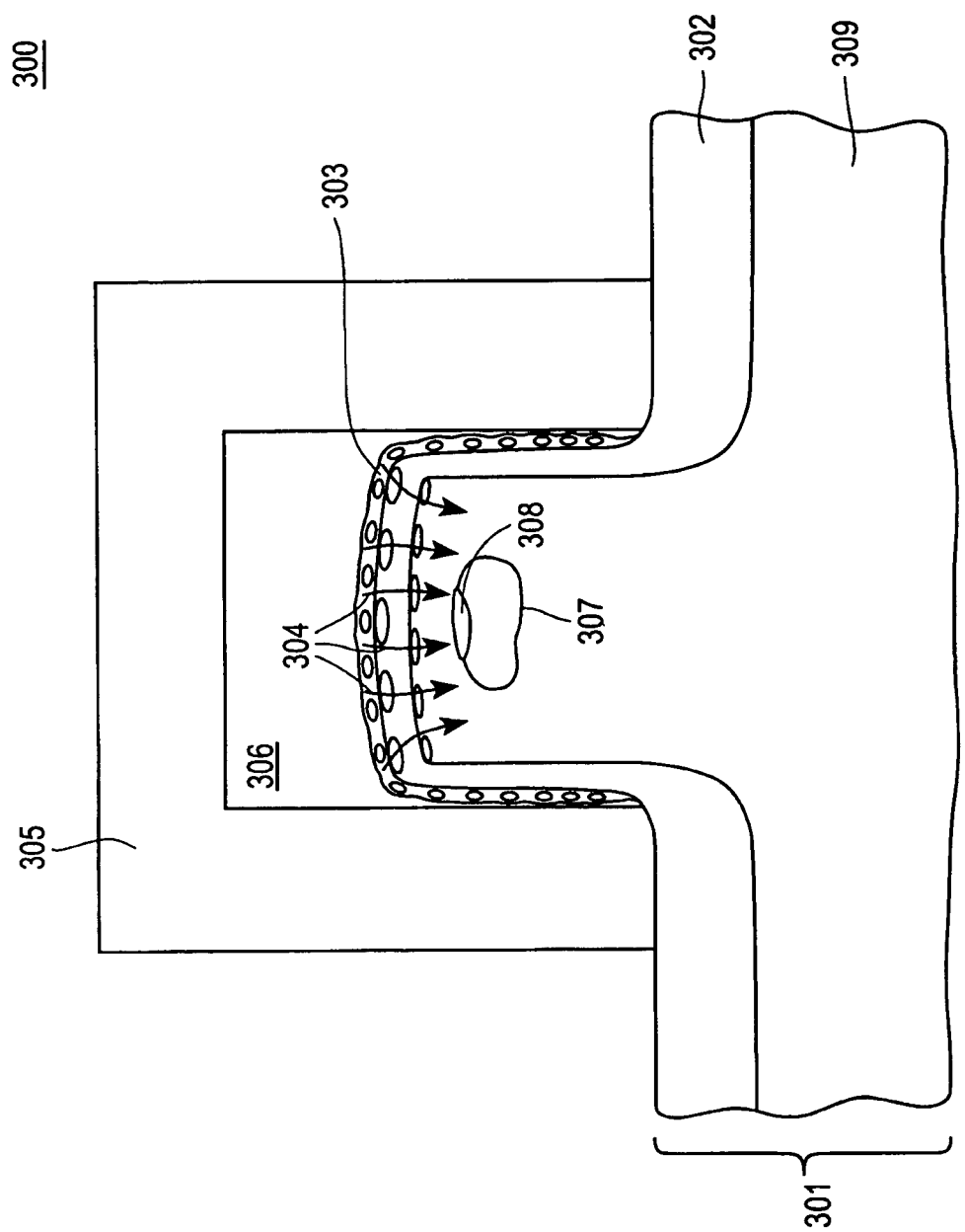
FIG. 3A is a cross-sectional view of one embodiment of a device to apply a substance into a biological tissue.

FIG. 3A is a cross-sectional view 300 of one embodiment of a device 305 to apply a substance into a biological tissue 301. As shown in FIG. 3A, device 305 having chamber 306 is applied to a surface of biological tissue 301. Biological tissue 301 may be an external biological tissue, e.g., a skin. Substance 303 is applied over the surface of biological tissue 301, which has upper portion 302, e.g., epidermis, and lower portion 309 containing target 307, as shown in FIG. 3A. Substance 303 may be applied to the biological tissue 301 before or after the biological tissue is stretched. Substance 303 applied to the biological tissue may be in any physical state, e.g., a gel, a cream, particles, a liquid, a mist, a gas, or any combination thereof. In one embodiment, substance 303 applied to the surface of the biological tissue 301 may be a medicine, a lotion, a moisturizer, a cleansing cream, or any other substance known to one of ordinary skill in the art of biological tissue treatment. In one embodiment, substance 303 may be applied to biological tissue through a substance supplier coupled to chamber 306. The substance supplier may be a conduit, a spray, a dispenser, a pad, or any other substance supplier known to one of ordinary skill in the art of biological tissue treatment. The embodiments of substance supplier is described in further details below with respect to FIGS. 10A and 10B.

Device 305 may be connected to a vacuum system, such that a negative pressure, e.g., a vacuum, is applied to chamber 306. For example, when device 305 is placed over the skin and a vacuum is applied, the skin is drawn into chamber 306 and stretched. As shown in FIG. 3A, the negative pressure pulls up at least a portion of biological tissue 301 into chamber 306, as shown in FIG. 3A. In one embodiment, the vacuum applied to biological tissue 301 corresponds to an air pressure less than 400 torr.

Biological tissue 301 is stretched by the negative pressure while substance 303 is applied over the surface of biological tissue 301, as shown in FIG. 3A. Stretching produces openings 304 in the surface of the biological tissue 301, as shown in FIG. 3A. In one embodiment, stretching of biological tissue 301 produces openings 304 and opening 308 in target 307, as shown in FIG. 3A. In one embodiment, the stretching process separates the epidermal structures of the skin whereby opening pathways for substance 303 to penetrate deeper into the epidermis. For example, the stretching of the skin opens the pores on the surface of the skin. Any substance placed on the pores while pores are open is drawn through the pores into the skin when the skin relaxes later on in the process. Further, target 307, e.g., a hair, a pigment, a vein, or a gland, e.g., a sebaceous gland, is lifted by the negative pressure and brought closer to the surface of biological tissue 301, as shown in FIG. 3A. In one embodiment, the stretching of biological tissue 301, e.g., a skin, pushes a sebaceous gland to the surface whereby exposing an inner surface of the sebaceous gland to the environment. Openings 304, e.g., pores, or ducts, provide pathways for substance 303 to penetrate deeper into biological tissue 302 and to target 307. Opening 308 in target 307 provides a pathway for substance 303 to penetrate into internal portion of target 307. In one embodiment, the skin is stretched and opened using the vacuum, such that an inner surface of the sebaceous gland is exposed. In one embodiment, while the skin is stretched, substance 303, e.g., a medicine, is applied to the sebaceous gland, such that substance 303 contacts inner walls of the sebaceous gland.

Because substance 303 is applied to biological tissue 301 while biological tissue 301 is stretched, substance 303 is drawn into biological tissue 301 when stretching is removed. This allows more of substance 303 to penetrate into biological tissue 301 to a greater depth, e.g., into and below epidermis, to reach one or more targets located in dermis and subcutaneous tissue of the skin that increases efficiency of substance 303.

Figure 3B:
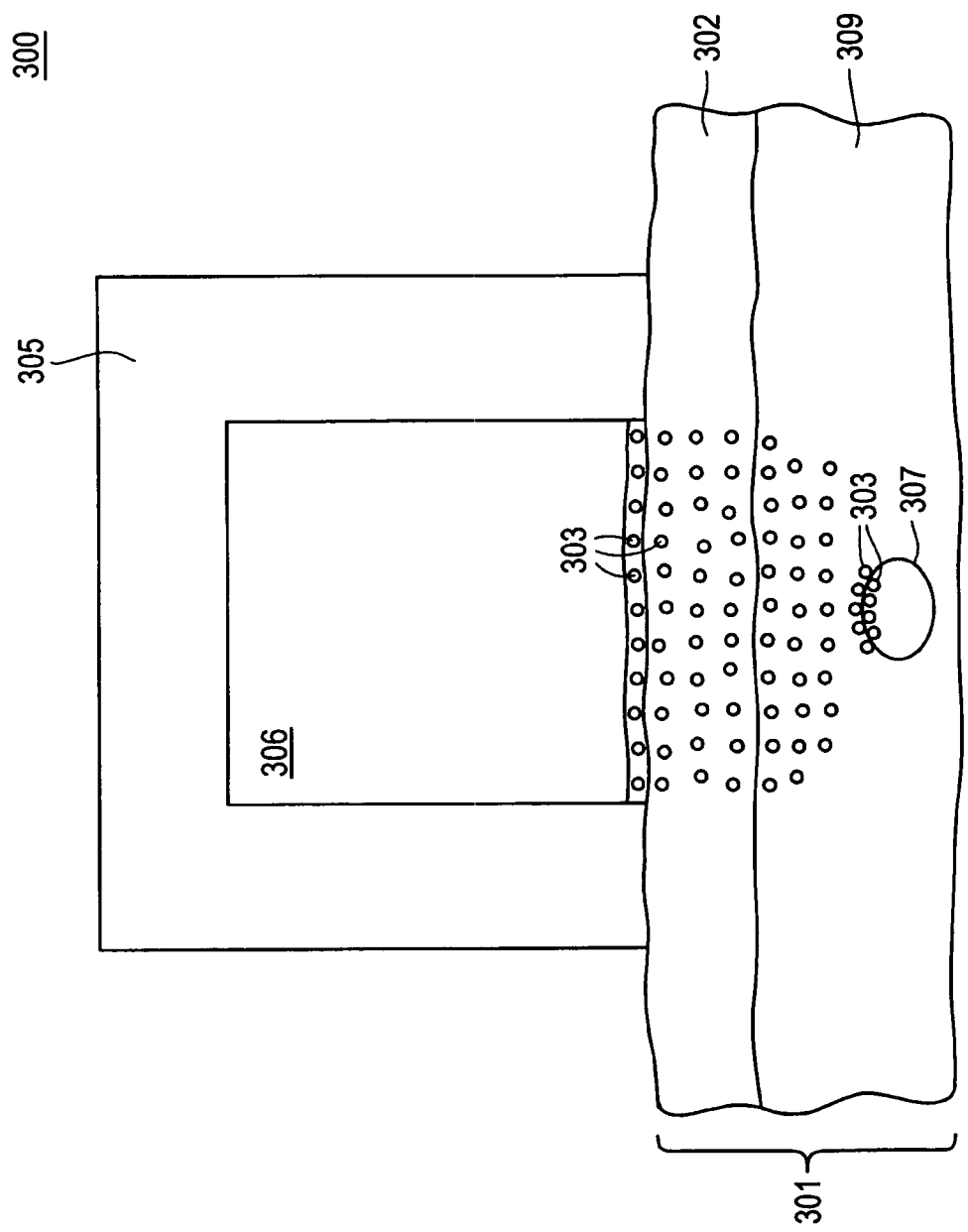
FIG. 3B is a view the device of FIG. 3A, after a negative pressure is removed according to one embodiment.

FIG. 3B is a view similar to FIG. 3A, after a negative pressure is removed according to one embodiment of the invention. As shown in FIG. 3B, biological tissue 301 is relaxed and target 307 returns to its original position below the surface of biological tissue 301. Substance 303 is penetrated deeply through openings 304 of FIG. 3A into upper portion 302 and lower portion 309 of biological tissue 301, as shown in FIG. 3B, due to removing a stretch from the biological tissue 301 produced by the negative pressure. In one embodiment, substance 303 is penetrated through opening 308 of FIG. 3A into an internal portion of target 307, as shown in FIG. 3B. As such, substance 303 lasts longer and is more effective, when it is penetrated into the biological tissue 301, as described above. For example, if substance 303 is a medicine, more of the medicine enters the skin and therefore the medicine is more effective. If substance 303 is a moisturizer, the beneficial effects of the moisturizer lasts longer because more of the moisturizer is penetrated the skin.

Figure 4:
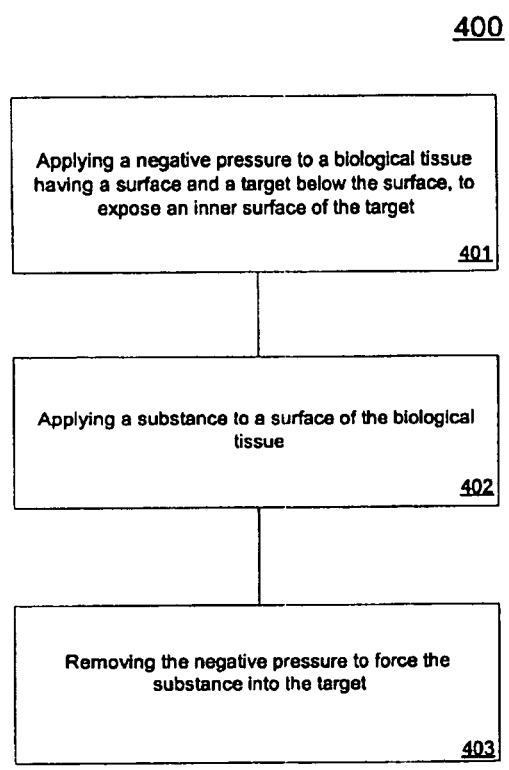
FIG. 4 is a flowchart of another embodiment of a method to treat a biological tissue.

FIG. 4 is a flowchart 400 of another embodiment of a method to treat a biological tissue. As shown in FIG. 4, the method begins with operation 401 of applying a negative pressure to a biological tissue having a surface and a target below the surface, as described above with respect to FIG. 3A. The applied negative pressure stretches the biological tissue creating openings 304 in the surface of the biological tissue 301 and opening 308 in target 307 such that inner surface of target 307 becomes exposed. Referring back to FIG. 4, the method continues with operation 402 of applying a substance to a surface of the biological tissue. As described above, the substance applied to the biological tissue may be a medicine, a lotion, a moisturizer, water, or any combination thereof. As shown in FIG. 4, the method further continues with operation 403 of removing the negative pressure to draw the substance into the target through openings 304 and opening 308, as described above with respect to FIGS. 3A and 3B. In one embodiment, before performing operation 401, a positive pressure is applied to provide the substance to the biological tissue, such that operation 402 may be skipped later on in the process. For example, when the positive pressure is applied to the biological tissue, one or more substances are sprayed out on to the surface of the biological tissue.

Figure 5A:
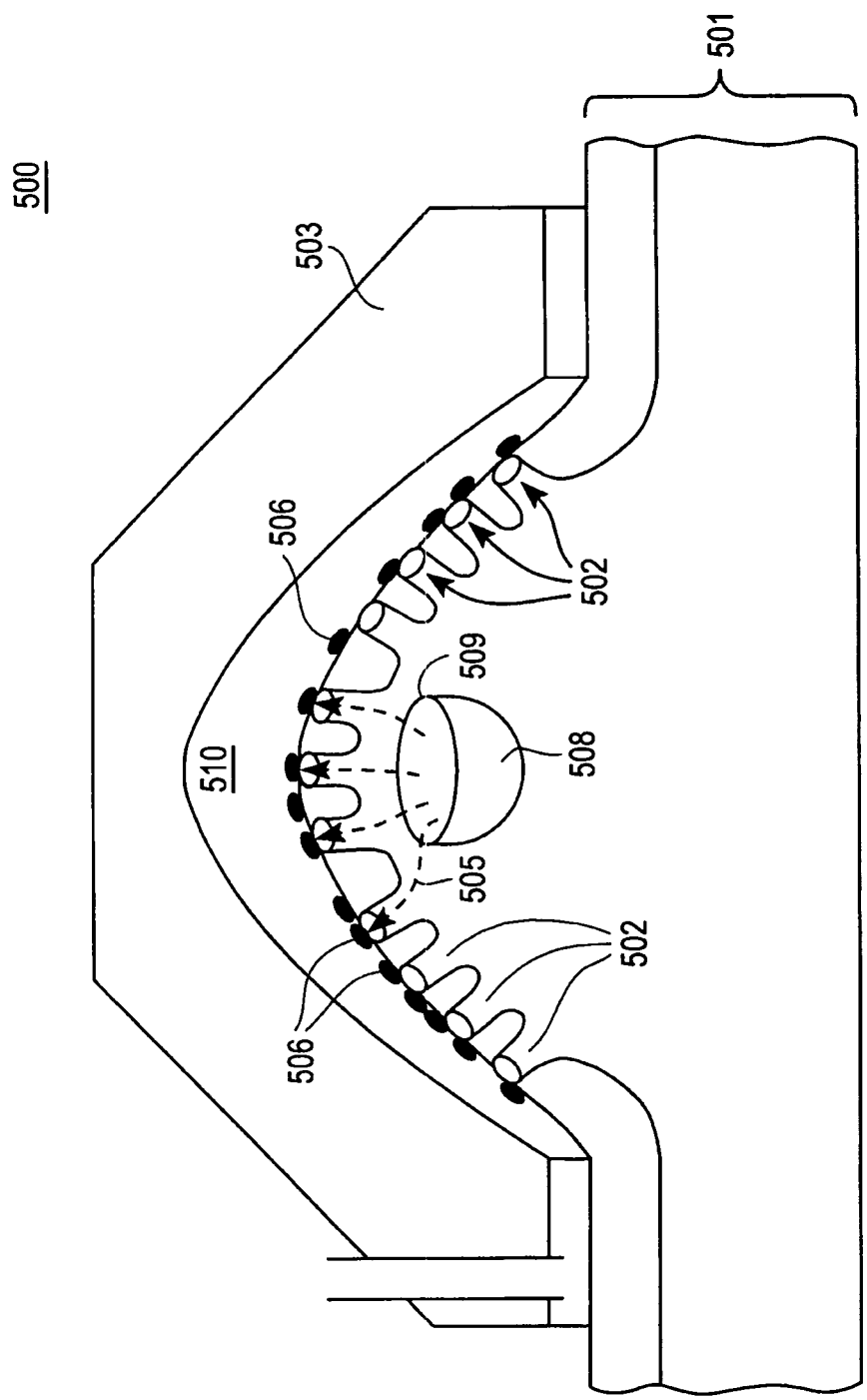
FIG. 5A is a cross-sectional view of one embodiment of a device to clean a biological tissue.

FIG. 5A is a cross-sectional view 500 of one embodiment of a device 503 to clean a biological tissue 501. As shown in FIG. 5A, device 503 having chamber 510 is applied to a surface of biological tissue 501. Biological tissue 501 may be an external biological tissue, e.g., a skin. A negative pressure, e.g., a vacuum is applied to chamber 510 that pulls up at least a portion of biological tissue 501 into chamber 510, as shown in FIG. 5A. The negative pressure stretches biological tissue 501 to produce openings 502 in the surface of biological tissue 501 and opening 509 in target 508 to clean out target 508, as shown in FIG. 5A. Stretching of biological tissue 501 is such that it forces a material 506 from target 508 through opening 509 and openings 502 onto the surface of biological tissue 501, as shown by dashed lines 505 in FIG. 5A. In one embodiment, target 508 is a sebaceous gland, and material 506 is a sebum, dead cells, and other debris. In one embodiment, device 503 connected to a vacuum system is applied to the surface of the skin for several seconds, for example, between 1 to 20 seconds. In one embodiment, an air pressure produced in chamber 510 is less than 400 torr. Negative pressure produced by device 503 opens up target 508, e.g., a sebaceous gland, to the surface of the skin, and pushes out material 506, e.g., sebum, dead skin cells, and other debris contained in target 508 onto the surface of the skin. In one embodiment, material 506 may be wiped off the surface of the biological tissue 501 with a cloth or other article which is known to one of ordinary skill in the art of biological tissue treatment. In one embodiment, material 506 is wiped off while the vacuum is still applied to biological tissue 501. In another embodiment, material 506 is wiped off after the vacuum is removed from biological tissue 501.

Figure 5B:
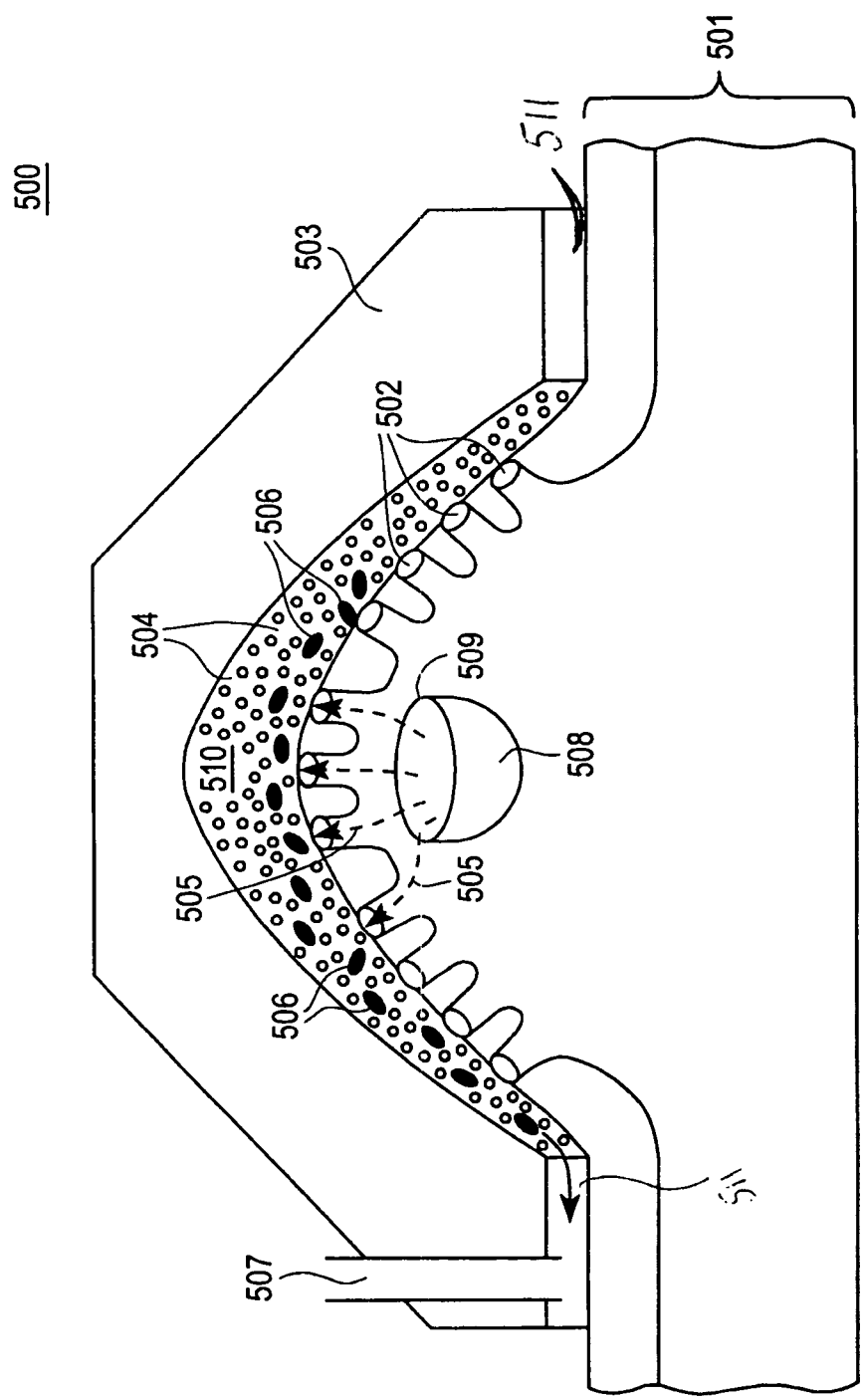
FIG. 5B is a view the device of FIG. 5A, after a substance is applied to promote cleaning of biological tissue according to one embodiment.

FIG. 5B is a view similar to FIG. 5A, after a substance 504 is applied to promote cleaning of biological tissue 501 according to one embodiment of the invention. As shown in FIG. 5B, substance 504 containing an abrasive material, e.g., aluminum oxide, is applied while biological tissue 501 is stretched. In one embodiment, biological tissue 501 is stretched by a negative pressure, as described above with respect to FIG. 5A. Stretching exposes material 506 in openings 502 and in opening 509. Stretching also forces material 506 from opening 509 through openings 502 onto the surface of biological tissue 501, as described above with respect to FIG. 5A, such that material 506 becomes easily removable by substance 504. Substance 504 applied to the stretched biological tissue 501 may easy remove material 506 from the surface of biological tissue 501. For example, an abrasive material applied to a skin, while the skin is stretched, improves skin exfoliation. An abrasive material is much more effective when the skin surface is stretched to be smooth and much of the debris from inside the pores is on the surface of the skin and can easily be removed with the abrasive material. In one embodiment, substance 504 is added to a spray and applied to biological tissue 501 while biological tissue 501 is stretched. In another embodiment, substance 504 is applied mechanically, e.g., by rubbing against biological tissue 501, e.g., a skin, while biological tissue 501 is stretched. In yet another embodiment, stretched biological tissue 501 is exposed to substance 504, e.g., an aluminum oxide powder, from a micro dermabrator. In yet another embodiment, abrasive material is applied to the edges 511 to chamber 510. These edges 511 contact the biological tissue when the chamber 510 is placed against the biological tissue. When biological tissue 501, e.g., skin, is pulled into chamber 510 by, e.g., a negative pressure, biological tissue 501 is scraped along the abrasive material performing an abrasion of biological tissue 501. As such, debris, e.g., dead surface skin, is abraded away from the surface of biological tissue 501.

In one embodiment, after cleaning the biological tissue 501 with substance 501, another substance, e.g. a lotion, a moisturizer, water, a medicine, or any other material may be applied to further treat biological tissue 501. The another substance may be applied to biological tissue for example, by spraying. In one embodiment, another substance may be applied while biological tissue 501 is stretched, as described below with respect to FIGS. 8 and 9.

FIG. 6 is a flowchart 600 of one embodiment of a method to clean a biological tissue, as described above with respect to FIGS. 5A and 5B. The method begins with operation 601 of applying a negative pressure to a biological tissue having a surface and a target under the surface, to push out at least a portion of a material from the target onto the surface of biological tissue. The method continues with operation 602 of applying a substance to the surface of the biological tissue while stretching to promote cleaning the biological tissue. In one embodiment, the substance is applied to the surface after the biological tissue is stretched. In another embodiment, after performing operation 601, the negative pressure is removed and the material from the target, e.g., dead cells, debris, sebum, and the like is wiped off the surface of the biological tissue using one of techniques known to one of ordinary skill in the art of biological tissue treatment. In one embodiment, after cleaning the biological tissue, for example, after the sebum, dead cells, the debris, and the like, material is removed from the surface of the biological tissue, the biological tissue, e.g., the target, may be then treated with one or more energies, e.g., light, radio frequency, or ultrasound. In one embodiment, the biological tissue may be treated with one or more energies after the negative pressure is removed. In another embodiment, the biological tissue may be treated with one or more energies while the biological tissue is stretched by the negative pressure. Embodiments of a device incorporating various energy sources to treat the biological tissue are described in further details below with respect to FIGS. 10A and 10B.

FIG. 7 is a flowchart 700 of another embodiment of a method to clean a biological tissue, as described above with respect to FIGS. 5A and 5B. The method begins with operation 701 of stretching a biological tissue having a surface to provide openings in the surface. The method continues with operation 702 of applying a substance to the surface while stretching to promote cleaning of the biological tissue. In one embodiment, the substance is applied to the surface after the biological tissue is stretched, to promote cleaning.

Figure 8:
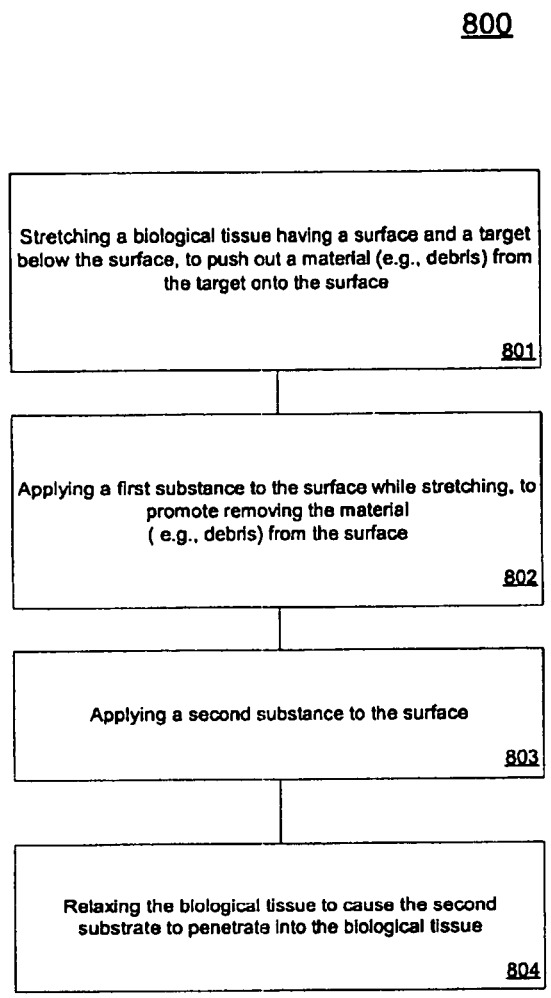
FIG. 8 is a flowchart of one embodiment of a method to treat a biological tissue.

FIG. 8 is a flowchart 800 of one embodiment of a method to treat a biological tissue, as described above with respect to FIGS. 3A-3B and 5A-5B. The method begins with operation 801 of stretching a biological tissue having a surface and a target below the surface, to push out a material, e.g., a debris, dead cells, sebum, and the like, from the target onto the surface of the biological tissue, as described above with respect to FIG. 5A. The method continues with operation 802 of applying a first substance to the surface of the biological tissue while stretching, to promote removing the material, e.g., a debris, dead cells, sebum, and the like, from the surface of the biological tissue. In one embodiment, the first substance contains an abrasive material, as described above with respect to FIG. 5B. Next, the method continues with operation 803 of applying a second substance to the surface of the biological tissue. Applying a second substance to the surface of the biological tissue is described in further details below with respect to FIGS. 10A and 10B. In one embodiment, the second substance is a medicine, a moisturizer, a lotion, or any combination thereof. Next, in operation 804, the biological tissue is relaxed to cause the second substance to penetrate into the biological tissue, as described with respect to FIGS. 3A and 3B.

FIG. 9 is a flowchart 900 of one embodiment of a method to treat a biological tissue, as described above with respect to FIGS. 3A-3B and 5A-5B. The method begins with operation

901 of applying a negative pressure to provide openings in a surface of the biological tissue, as described above with respect to FIG. 5A. Next, the operation 902 of exposing the surface of the biological tissue to a first substance while stretching to promote cleaning (e.g., exfoliation) of the biological tissue is performed, as described above with respect to FIG. 5B. In one embodiment, the first substance contains an abrasive material, as described above with respect to FIG. 5B. The method continues with operation 903 of applying a second substance to the surface of the biological tissue while the biological tissue is stretched. In one embodiment, the second substance is a medicine, a moisturizer, a lotion, as described above with respect to FIG. 3A. Next, operation 904 of removing the negative pressure to push the second substance through the openings into the biological tissue is performed, as described above with respect to FIG. 3B.

Figure 10A:
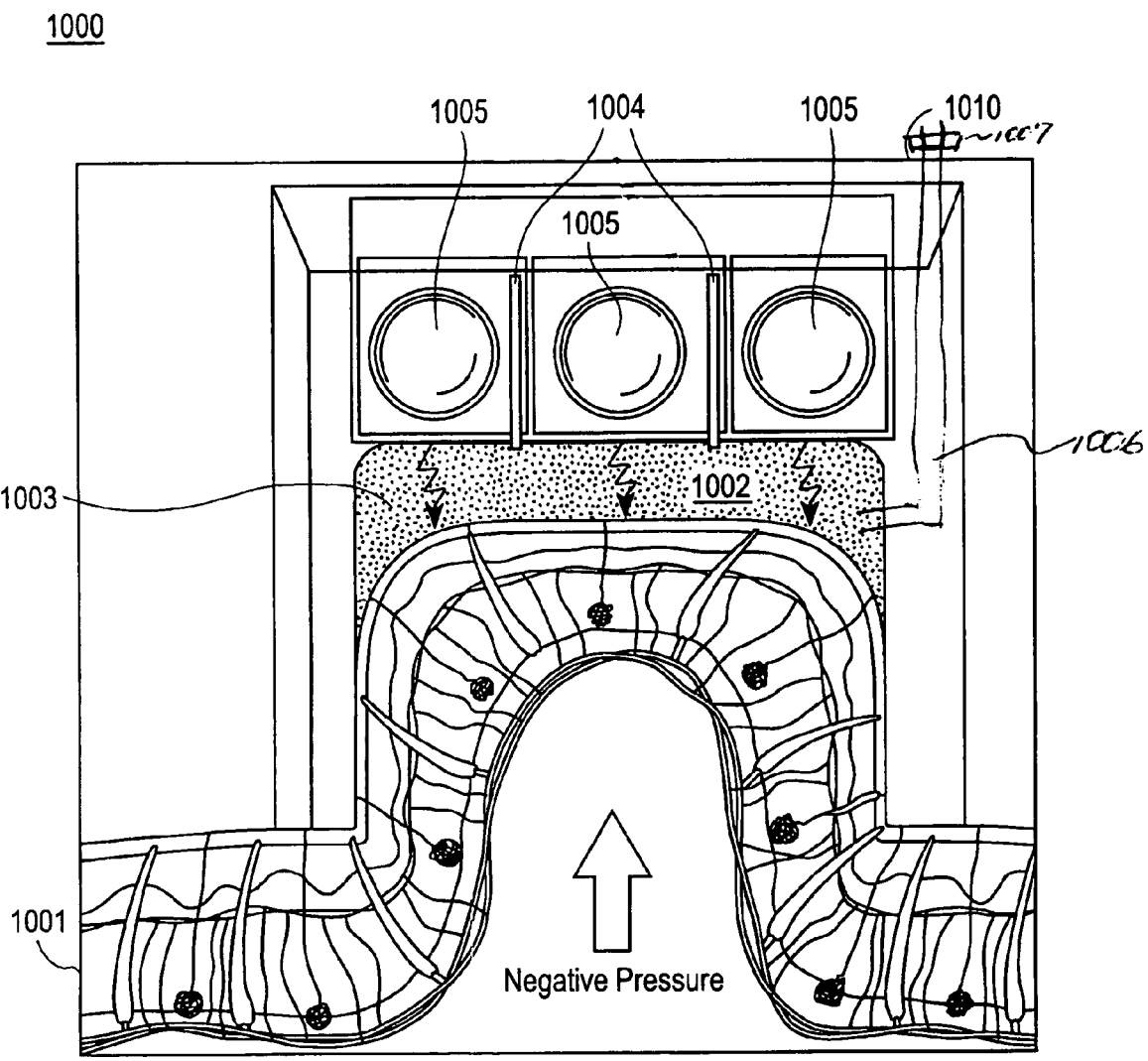
FIG. 10A is a cross-sectional view of one embodiment of a device having a substance supplier and energy sources, to treat a biological tissue.

FIG. 10A is a cross-sectional view 1000 of one embodiment of a device 1000 having a substance supplier 1004, to treat a biological tissue 1001. As shown in FIG. 10A, device 1010 has a chamber 1002, wherein a mist 1003 containing a substance is supplied through at least one substance supplier 1004 (e.g., a conduit) coupled to chamber 1002. As shown in FIG. 10A, biological tissue 1001 is stretched by applying a negative pressure and mist 1003 containing the substance is sprayed into the evacuated chamber 1002 having lifted up biological tissue 1001. For example, skin is pulled into an evacuated chamber 1002 where mist 1003 containing the substance is applied, as shown in FIG. 10A. In one embodiment, the substance in substance supplier 1004 is under positive pressure (e.g. air pressure pushes the substance out of the conduit and into the chamber). In one embodiment, device 1010 may include at least one pressure conduit (not shown), for example, at least one tube coupled to chamber 1002, which provides a positive pressure. Such conduit may be used to apply the substance to biological tissue 1001 and/or to force biological tissue 1001 out of chamber 1002, when the negative pressure is removed. In another emodiment, device 1010 may include at least one conduit 1006, for example, at least one tube coupled to chamber 1002, which utilizes the negative pressure in chamber 1002 to pull the substance to biological tissue 1001. The substance may be pulled out of the subtance supplier 1004 by the negative pressure and applied to stretched biological tissue 1001 through the effect of the vacuum. Subtance supplier 1004 may be connected to one or more subtance reservoirs (not shown) and to chamber 1002. When the negative pressure is applied to the chamber 1002, the substance is drawn into the chamber and onto biological tissue 1001. Valve 1007 coupled to conduit 1006 may control the timing of the application of the substance and quanity of the substance to biological tissue 1001.

In one embodiment, as shown in FIG. 10A, device 1010 has at least one energy source 1005, which may be activated at any time, e.g., before, during, or immediately after applying the substance to biological tissue 1001. In one embodiment, as shown in FIG. 10A, the energy sources are activated when biological tissue 1001 is stretched by the negative pressure and when substance 1003 is applied to biological tissue 1001. Energy source 1005 may be a coherent light source, or non-coherent light source, as shown in FIG. 10A. In alternate embodiments, energy source 1005 may be a coherent light source, a non-coherent light source, a radio frequency source ("RF source"), an ultrasound source, or any combination thereof. In an embodiment, as shown in FIG. 10A, energy source 1005 is separated from chamber 1002 by a cover to avoid an exposure to any pressure inside the chamber 1002.

Figure 10B:
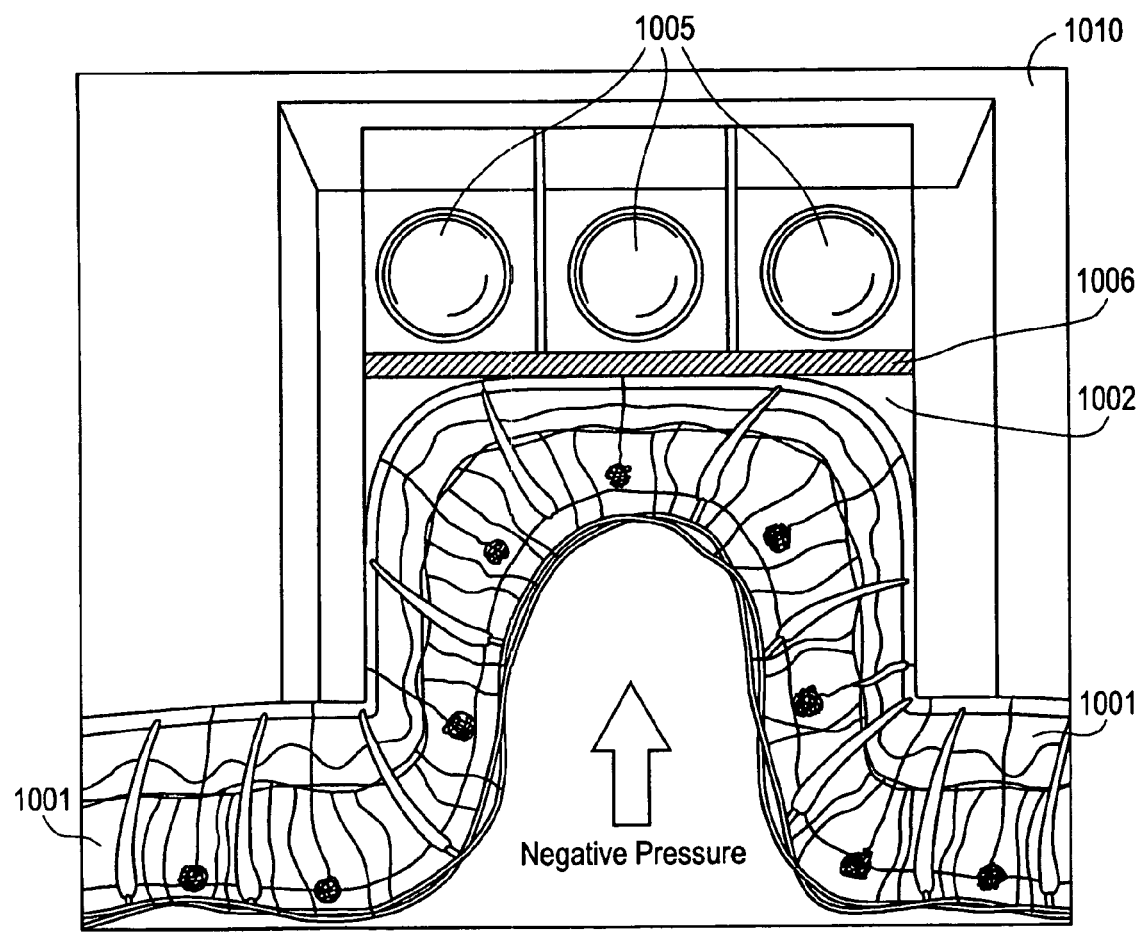
FIG. 10B is a cross-sectional view of another embodiment of a device having a substance supplier and energy sources, to treat a biological tissue.

FIG. 10B is a cross-sectional view 1020 of another embodiment of a device 1010 having a substance supplier 1006, to treat a biological tissue 1001. As shown in FIG. 10B, device 1010 has chamber 1002, wherein biological tissue 1001 is pulled up against a pad ("substance supplier 1006") containing a substance. By pressing against the pad, e.g., a porous sponge, the substance is applied to biological tissue 1001, as shown in FIG. 10B. As shown in FIG. 10B, the substance may be applied by pressing biological tissue 1001, e.g., a skin, against substance supplier 1006, which may be a pad containing a porous sponge like material that secrets the substance on to biological tissue 1001. By pressing the biological tissue 1001 against substance supplier 1006, the biological tissue 1001 is stretched, such that pores in the biological tissue 1001 are opened, and the substance is "pushed" into biological tissue 1001. Biological tissue 1001 may be pressed against the supplier 1006 by forming a vacuum in chamber 1002 and against substance supplier 1006. Biological tissue 1001 is then allowed to relax by releasing the vacuum in chamber 1002, causing biological tissue 1001 to relax.

Figure 11:
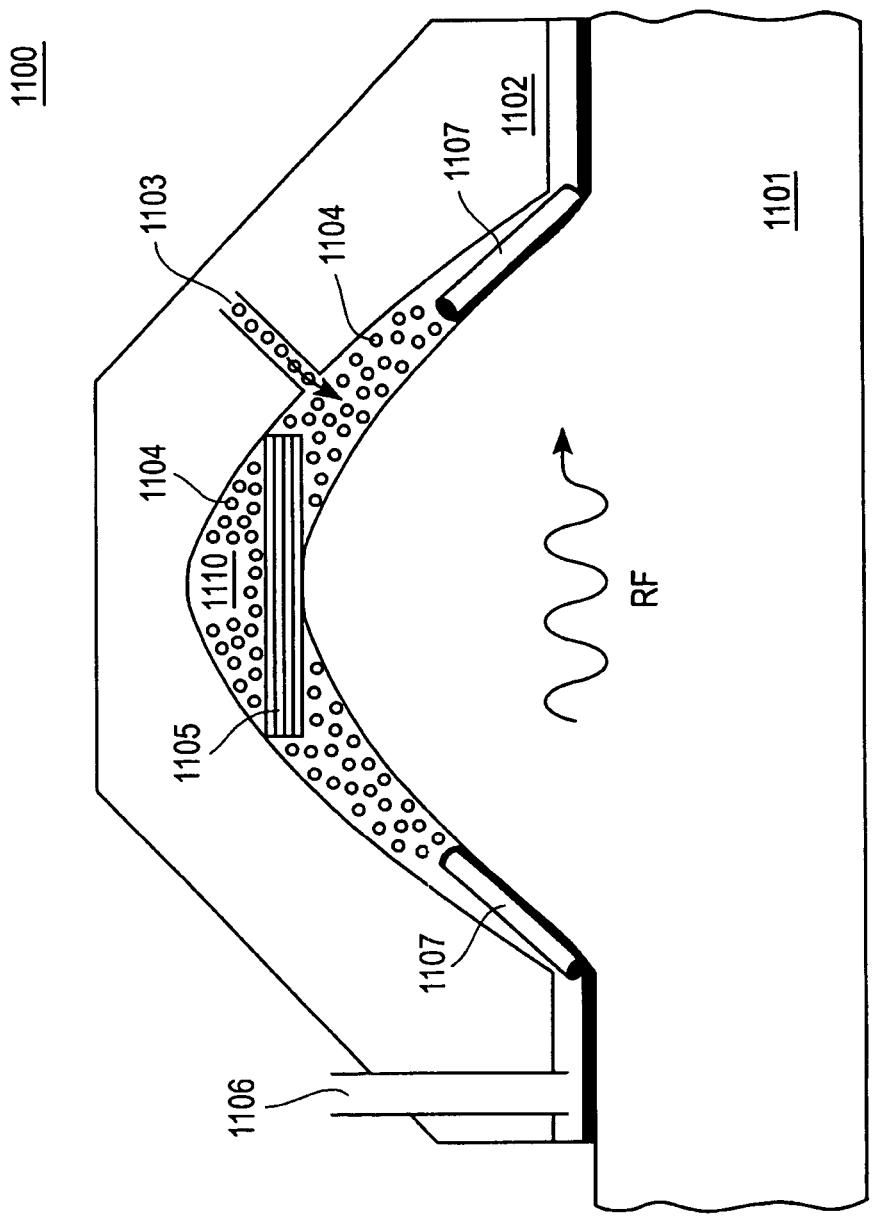
FIG. 11 is a cross-sectional view of one embodiment of a device having RF energy sources, to treat a biological tissue.

FIG. 11 is a cross-sectional view 1100 of another embodiment of a device 1102 having RF energy sources 1107, to treat a biological tissue 1101. As shown in FIG. 11, a negative pressure, e.g., vacuum, is supplied to a chamber 1110 of device 1102 through a pressure conduit 1106 to open, e.g., pores or ducts, in biological tissue 1101. Pressure conduit 1106 may also be used to generate a positive pressure, e.g., to remove vacuum from chamber 1110. As shown in FIG. 11, conduit 1103 may supply a substance 1104 to chamber 1110, as described above with respect to FIGS. 10A and 10B. As shown in FIG. 11, RF energy sources 1107, which are coupled to device 1102, provide RF energy to biological tissue 1101. In alternate embodiments, RF energy sources 1107 may be activated at any time relative to applying the negative pressure and substance 1104 to biological tissue 1101.

As shown in FIG. 11, an article 1105 coupled to device 1102, may be brought into contact with biological tissue 1101 to press onto biological tissue 1101 and force the blood out of the contact area, to reduce blood concentration in biological tissue 1101 below a contact area. Article 1105 may be stationary relative to biological tissue 1101, or it may move, like a plunger or piston, toward biological tissue 1101. In alternate embodiments, article 1105 may be applied to biological tissue 1101 either before, or in the same time as the negative pressure through pressure conduit 1106 is applied, thereby drawing the biological tissue into chamber 1110 and into contact with article 1105. In one embodiment, a cooling substance, e.g., a cooling gas, may be supplied to chamber 1110 to reduce a temperature of biological tissue 1101 during a treatment. The cooling substance may be provided to chamber 1110 by conduit 1106, 1103, or an additional conduit (not shown).

Figure 12:
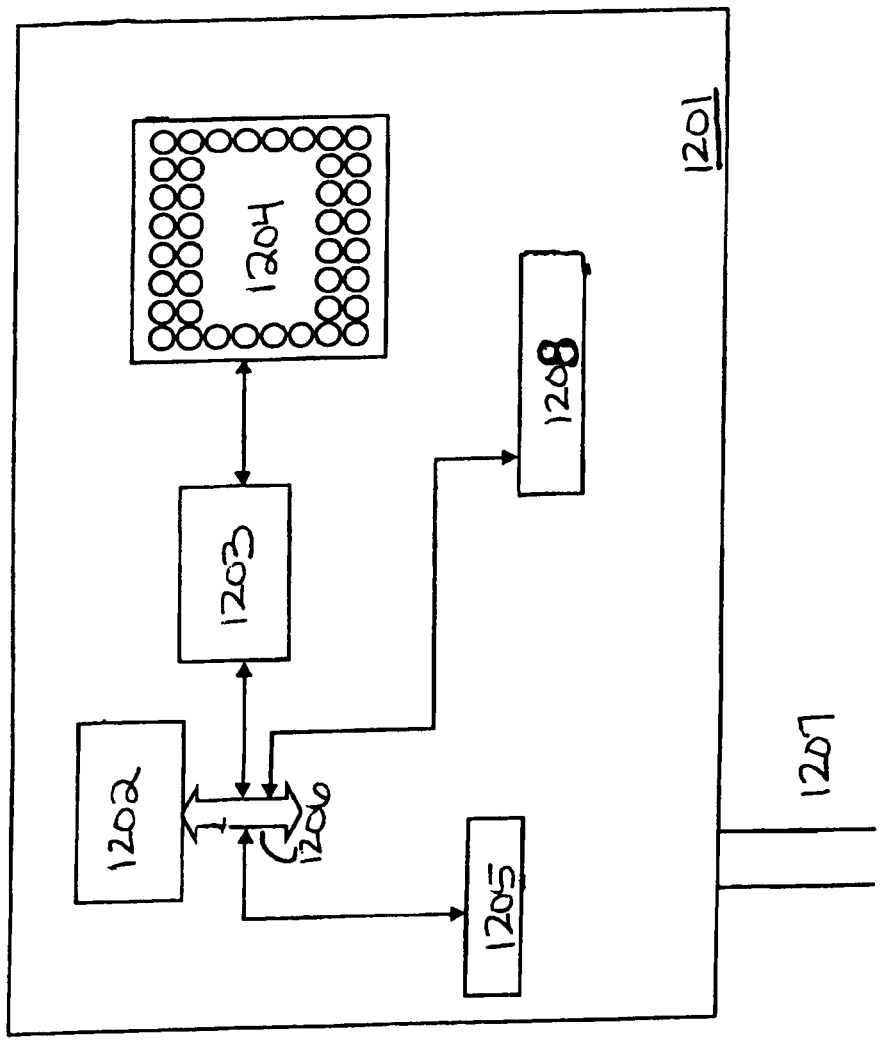
FIG. 12 is an electrical block diagram of one embodiment of a device to apply a substance to treat a biological tissue.

FIG. 12 is a block diagram 1200 of one embodiment of a device to apply a substance to treat a biological tissue as described above with respect to FIGS. 2-11. A device 1201, as shown in FIG. 12, includes an LCD display 1204 coupled to a micro controller 1202 through a display controller 1203, as shown in FIG. 12. It will be appreciated that display controller 1203 may be eliminated if the micro controller performs the display updating functions of the display controller. Micro controller 1202 is coupled to one or more sensors 1205 and to one or more energy sources 1208 through a bus 1206, as shown in FIG. 12. Sensors 1205 may be electrical sensors, e.g., electrodes attached to the skin, mechanical sensors, photodetectors, electromechanical sensors, or any other sensors known to one of ordinary skill in the art of biological tissue treatment. Sensors 1205 may include a pressure sensor to determine a level of the pressure in the chamber, a vapour pressure sensor, to control a level of a vaporizing substance, a sensor to determine an amount of applied substance, a sensor to determine a temperature in the chamber, a temperature of the biological tissue, a skin color, a motion sensor, e.g., to control moving the biological tissue, or any other sensor to operate skin treatment device. The energy sources 1208 may be multiple light sources and/or radio frequency electrical electrodes and/or other types of energy sources described herein and/or a combination of these sources. Device 1201 may include a supply 1207, to provide an electrical power, to connect to vacuum pump and air pump. Micro controller 1202 may be programmed to operate device 1201 automatically in one or more of the methods described herein.

Figure 13:
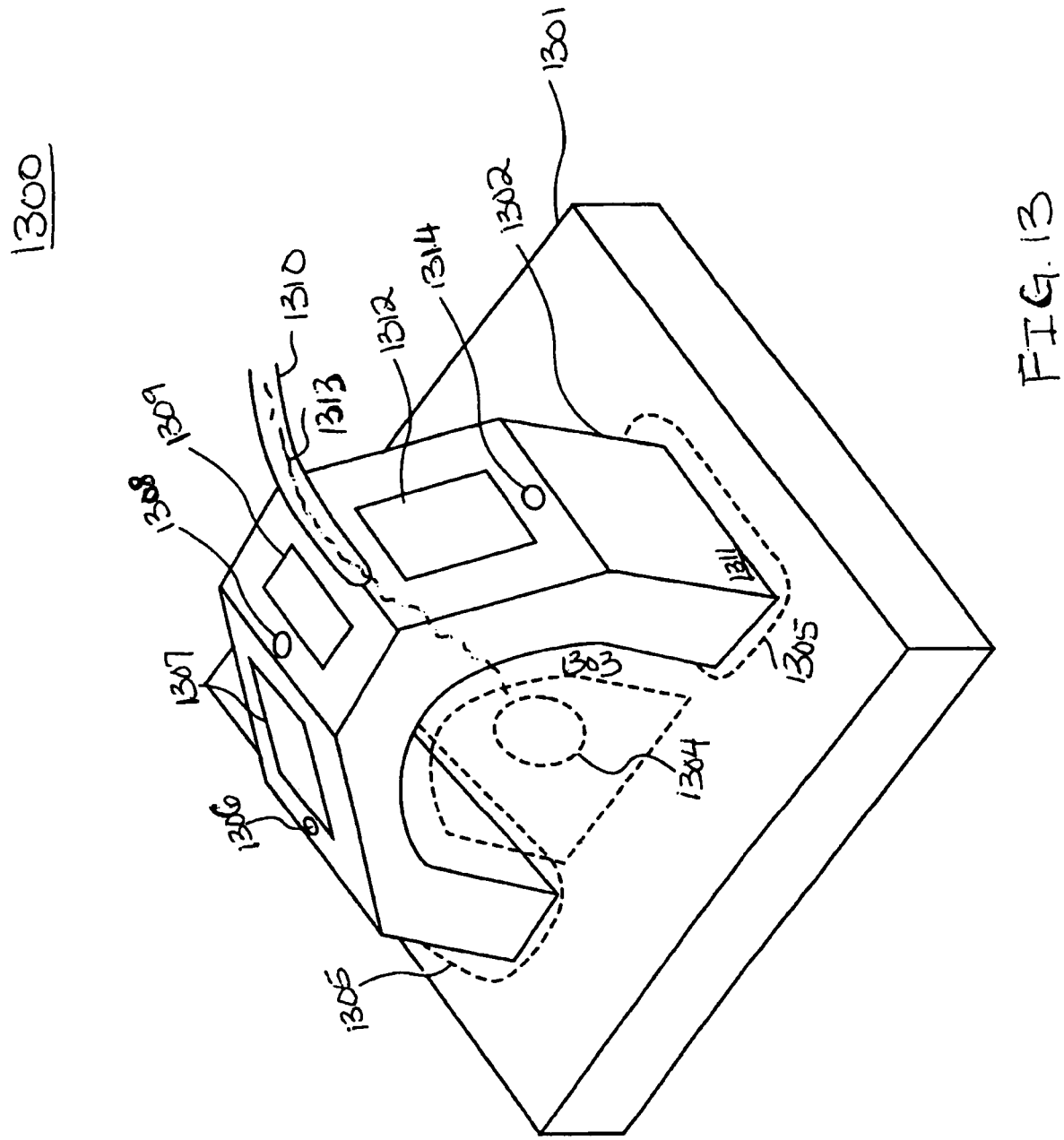
FIG. 13 is a cutaway view of a handheld device of one embodiment of the invention.

FIG. 13 is a cutaway view 1300 of a device 1302 to treat a biological tissue 1301 according to one embodiment. As shown in FIG. 13, device 1302 has an outer portion 1311 and a cavity 1303 encompassed by the outer portion 1311. Device 1302 is applied over biological tissue 1301, such that vacuum seals 1305 are formed between outer portion 1311 and biological tissue 1301. As shown in FIG. 13, chamber 1303 has a pressure below atmospheric pressure, such that at least a portion of biological tissue 1301 having target 1304 is brought into chamber 1303.

As shown in FIG. 13, a substance supplier 1310, e.g., a conduit, provides substance 1313 to chamber 1303 to apply to biological tissue 1301, as described herein. In an embodiment, device 1302 has one or more ports to provide negative and positive pressures or substances to chamber 1303, e.g., port 1306, port 1308, and port 1314. As shown in FIG. 13, outer portion 1311 of device 1302 may have one or more panels, e.g. panels 1307, 1309, and 1312, connected to respective energy sources (not shown), sensors (not shown), and power regulators (not shown) to display data and information on operation of device 1302. In one embodiment, device 1302 may be programmed to automatically adjust pressure and an amount of substance 1313 in chamber 1303. In one embodiment, device 1302 is a portable device.

Figure 14:
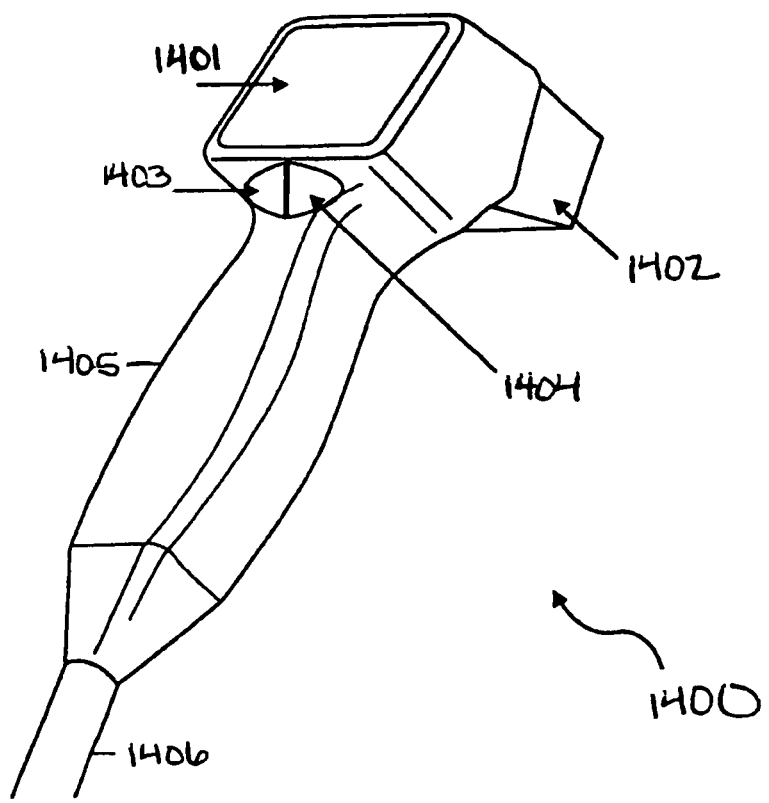
FIG. 14 is a perspective view of a handheld device of an embodiment of the invention.

FIG. 14 is a perspective view of a handheld device 1400 to apply a substance to biological tissue according to one embodiment. It is appreciated that device 1400 may include one or more features described herein, e.g., substance suppliers, energy sources, pressure conduits, articles to push blood out of the treatment area, and sensors. As shown in FIG. 14, device 1400 includes a pixilated display with multiple rows and columns of pixels that may display a status of the device (e.g., "Standby" or "On" or "Treating"), a energy source status (e.g., Low or Medium or High, along with a bar graph), a vacuum status (e.g., "Low" or "High"), the skin's temperature, the skin's color, and the patient's pulse count. In an embodiment, display 1401 may be a liquid crystal display ("LCD"), or a light emitting diode ("LED") display. Device 1400 may have a power adjustment control 1404 to control the amount of energy that is applied to the biological external tissue (e.g., to adjusting the intensity of the light from light sources). The device 1400 also includes a pneumatic adjustment control 1403 to control a level of a vacuum that is applied from a vacuum pump (not shown) to a chamber of the device. Device 1400 may include a substance quanity adjustment control that may be used to regulate the amount of medicine, lotion, or other substance that is adminstrated in the procedure. Device 1400 includes a cable 1406 to provide power and pressures for device operation. For example, cable 1406 may include one or more electrical wires to connect device 1400 to an electrical outlet, and one or more conduits to provide negative and positive pressure to a chamber of device 1400. As shown in FIG. 14, device 1400 has a tip 1402, which contains a chamber, which is applied to a biological tissue. In one embodiment, tip 1402 may be disposable. Cable 1406 may provide electrical connection to a standalone central control station (not shown). In one embodiment, the standalone central control station may be a computer that has a printer and/or storage device(s) for storing data provided by device 1400. In one embodiment, disposable tip 1402 on device 1400 may be a disposable membrane and may be custom designed to fit a particular type and a size of a biological tissue. For example, disposable tip 1402 may have a different size for large areas of a biological tissue versus small areas of biological tissue, and may be shaped differently in accordance with contours of a biological tissue. The handle 1405 of device 1400 may be designed to fit a particular size of hand and may have groves to fit a particular hand size in some embodiments.

The entirety of the U.S. patent application Ser. No. 11/024,340, filed on Dec. 27, 2004 is incorporated herein by reference.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A system to treat a biological tissue, comprising:
 means for stretching a biological tissue having a substance on a surface and a target below the surface; and
 means for relaxing the biological tissue to draw the substance from the surface into the biological tissue; and
 wherein the means for stretching comprises:
 a vacuum source;
 a vacuum conduit within a housing, the vacuum conduit coupled to the vacuum source;
 a controller coupled to the vacuum source to apply a vacuum to stretch the surface; and
 wherein the housing includes a first substance supplier through which the substance is applied onto the surface of the biological tissue and wherein the housing has an opening to receive the biological tissue; and
 wherein the means for relaxing comprises the controller which is configured to stop applying the vacuum to remove the stretching of the surface of the biological tissue after the substance is applied onto the surface; and
 wherein the controller coupled to the vacuum source is configured to apply the vacuum to stretch the surface that includes an epidermis that opens pathways in the epidermis, and exposes an inner surface of the target including sebaceous glands through the pathways, and wherein the controller is configured to provide the stretching that when removed generates a force that pushes the substance from the epidermis further down to the sebaceous glands.

2. The system of claim 1, wherein the vacuum is less than 400 torr.

3. The system of claim 1, wherein the substance, contained in the first substance supplier, is a medicine, a moisturizer, water, an alcohol, a lotion, or any combination thereof.

4. The system of claim 1 further comprising
 means for applying an energy to the biological tissue.

5. The system of claim 4, wherein the energy is a light, a radio frequency, an ultrasound, or any combination thereof.

6. The system of claim 1, further comprising
 means for providing a positive pressure to apply the substance onto the surface of the biological tissue.

7. The system of claim 1, wherein the system to treat the biological tissue comprises a handheld system.

8. A system to treat a biological tissue, comprising:
a vacuum system configured to create a vacuum to stretch a biological tissue having a surface and a target below the surface, to provide openings in the surface, wherein the surface includes an epidermis, and the target includes sebaceous glands;
a substance conduit configured to apply a first substance to the surface while stretching the surface to promote cleaning of the surface;
means for applying a second substance to the surface;
a housing coupled to the substance conduit and to the vacuum system, the housing having an opening to receive the surface while it is stretching;
a controller coupled to the vacuum source, wherein the controller and the vacuum source are configured to apply a sufficient vacuum to stretch the surface in order to open pathways in the epidermis and in order to expose inner surfaces of sebaceous glands through the pathways and wherein the controller is configured to stop applying the vacuum to the surface to remove the stretching of the surface, after the first substance is applied, in order to relax the surface, wherein the controller is configured to provide the stretching that when removed provides a force that pushes the second substance from the epidermis further down to the sebaceous glands.

9. The system of claim 8, wherein the first substance includes an abrasive material.

10. The system of claim 8, wherein the second substance is a medicine, moisturizer, water, an alcohol, a lotion, or any combination thereof.

11. The system of claim 8, wherein the vacuum is less than 400 torr.

12. The system of claim 1, the system further comprising a pressure sensor coupled to the controller and wherein the controller and the pressure sensor are configured to sense a positive pressure when the housing is applied to the surface and the controller is configured, in response to the sensing of the positive pressure, to apply the vacuum to the surface.

13. The system of claim 8, the system further comprising a pressure sensor coupled to the controller and wherein the controller and the pressure sensor are configured to sense a positive pressure when the housing is applied to the surface and the controller is configured, in response to the sensing of the positive pressure, to apply the vacuum to the surface.

14. The system of claim 5 wherein the energy is a light energy produced by a handheld system, and the system to treat the biological tissue comprises the handheld system and wherein the controller is configured to cause the means for applying the energy to apply the light energy before the substance is applied onto the surface of the biological tissue.

15. The system of claim 8 further comprising:
a light source coupled to the housing, the light source being configured to generate light to treat the biological tissue; and wherein the system to treat the biological tissue comprises a handheld system through which the light is applied to treat the biological tissue and through which the first substance is applied to the biological tissue.

16. The system of claim 1, wherein the controller is configured to apply the vacuum that lifts the target up from a first position below the surface to a second position closer to the surface.

17. The system of claim 1, wherein the first substance supplier is a pad against which the biological tissue is pulled up when the vacuum is applied.

18. The system of claim 1, wherein the first substance supplier is a conduit.

19. The system of claim 1, wherein the housing includes a second substance supplier.

20. The system of claim 1, further comprising an article coupled to the housing to reduce a blood concentration in the biological tissue.

21. The system of claim 8, wherein the controller is configured to apply the vacuum that lifts the target up from a first position below the surface to a second position closer to the surface.

22. The system of claim 8, wherein the first substance supplier is a pad against which the biological tissue is pulled up when the vacuum is applied.

23. The system of claim 8, wherein the first substance supplier is a conduit.

24. The system of claim 8, further comprising a substance supplier for the second substance.

25. The system of claim 8, further comprising an article coupled to the housing to reduce a blood concentration in the biological tissue.

26. The system of claim 13, wherein the substance includes one of a benzoyl peroxide, a salicylic acid, an azelaic acid, a sulfacetamide-sulfer, and an erythromycin.

* * * * *